Figure 1:
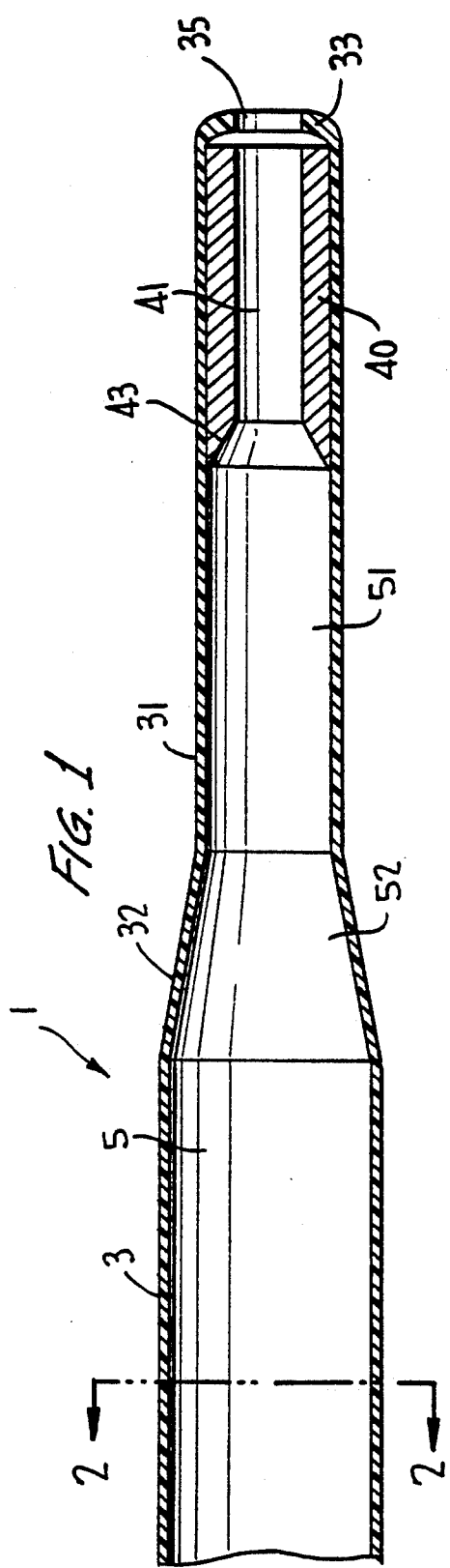

United States Patent [19]

Cannon

[11] Patent Number: 5,324,285
[45] Date of Patent: Jun. 28, 1994

[54] LASER-CATHETER

[75] Inventor: Robert L. Cannon, Conlie, France

[73] Assignee: C.B.A. Moulin de Classé, France

[21] Appl. No.: 50,730

[22] Filed: Oct. 15, 1992

Related U.S. Application Data

[63] Continuation of Ser. No. 623,909, Feb. 12, 1991, abandoned.

[30] Foreign Application Priority Data

Apr. 28, 1989 [FR] France ................... 89 05759

[51] Int. Cl.⁵ .............................................. A61N 5/06
[52] U.S. Cl. ......................................... 606/15; 606/10
[58] Field of Search .................................... 606/6–18; 607/88, 89

[56] References Cited

U.S. PATENT DOCUMENTS 4,526,170  7/1985  Tanner ........................ 128/398

FOREIGN PATENT DOCUMENTS 31073    7/1981  European Pat. Off. ............. 606/15
3718139 12/1988  Fed. Rep. of Germany ........ 606/15
11818   12/1989  World Int. Prop. O. ............ 606/16

Primary Examiner—David M. Shay
Attorney, Agent, or Firm—Breiner & Breiner

[57] ABSTRACT

A catheter is described including at least one optic fiber guided inside a tubular unit. The optic fiber is movable in the tubular unit between an active position wherein the fiber can transmit laser radiation energy and an inactive position wherein the fiber is retracted into the tubular unit. The fiber when retracted clears a duct which is present in the tubular unit. When the optic fiber is retracted a guide filament, which can also be present in the tubular unit, can then move in the duct. The fiber can include a stop which cooperates with another stop present in the tubular unit so as to ensure accurate positioning of the end of the fiber relative to the catheter. The catheter is useful in ridding blood vessels or other cavities of the human body of obstructions.

11 Claims, 1 Drawing Sheet

LASER-CATHETER

This is a continuation of co-pending application Ser. No. 07/623,909 filed on Feb. 12, 1991.

The invention concerns a catheter comprising an optic fiber or a bundle of fibers inside a flexible tubular unit whereby laser energy can be applied to destroy tissue obstructing a blood vessel or other cavity of the human body.

It is known to use a laser as the energy source in destroying specific targets in the body. The first $CO_2$ laser scalpels are known from 1960, and so are their coupling methods to fiber optics light guides.

The objects of this kind of treatment are urinary, biliary and parotid calculi, heart-valve calcification, pulmonary embolisms and various vascular obstructions. Among the latter, coronary-artery thromboses and stenoses are prominent.

The second generation apparatus makes use of a tip-heating method whereby the laser energy no longer is directly applied to the lesion but to a metal tip heated to a high enough temperature to melt the tissues. As the heat radiates in all directions, however, undesirable secondary effects take place caused by charring the healthy tissues.

The most recent approach uses pulsed lasers of which each pulse can vaporize a fine layer of tissue of about 6 to 10 microns and as a result the depth of penetration can be controlled by the number of pulses produced. From the European patent document 195,375, a laser catheter is known which comprises an optic fiber or a bundle of fibers inside a catheter ending in a transparent protecting screen. Aiming is carried out through this screen of which the distance at the distal end of the optic fiber determines the size of the luminous impact.

This catheter is activated by moving the screen into contact with the zone to be treated. In this manner the blood shall not interfere between the laser end and the target by causing undesired reactions. Also, a predetermined constant spacing is assured between the tip of the optic fiber and the said zone, whereby the energy magnitude applied to it can be better controlled. However, on account of said spacing, which is a feature of the aforementioned patent, the catheter diameter is significantly larger than that of the optic fiber it contains. It follows that this design appears to preclude apparatus with access to small-diameter vessels and to advance deeply inside the treated zone. Also, much complexity would be entailed when it is desired to incorporate a catheter guide means.

The object of the invention is a laser catheter simultaneously providing a distal end with a diameter as close as possible to that of the optic fiber and means allowing precise guidance toward the zone of operation so as to move the end of the optic fiber to the desired site and in particular in contact with the lesion to be treated.

In the invention, the catheter is characterized in that the optic fiber is movable inside the tubular unit between an active position wherein it can transmit light energy to the substance receiving treatment and an inactive position wherein it is retracted from the distal end of the tubular unit and where it clears a duct allowing in particular passage to a guide filament or wire.

Accordingly, the apparatus of the invention employs known techniques to accurately position the catheter, namely the preliminary insertion of a guide filament into the cavity as far as the lesion, then the advance of the catheter coaxially with the guide filament as far as the same site.

The duct in the distal end region serves to pass either the guide filament or the optic fiber. Thus, the catheter is optimally compact and the end of the optic fiber can reliably be advanced as far as necessary to make contact with the lesion and to avoid vaporizing blood between the stones or healthy tissue.

Another object of the invention is to provide a catheter of which the optic-fiber position can be determined in simple and accurate manner. This is achieved by providing a first stop rigidly affixed to the optic fiber and a second stop rigidly affixed to the tubular unit, both being mutually cooperating in order to lock the optic fiber in an axial direction of the tubular unit.

Thanks to this system, the optic fiber can be put in place in simple and accurate manner relative to the tubular unit of which the position was previously determined in relation to the lesion.

In a particular embodiment mode, the first stop consists of the downstream end of the sheath cladding the optic fiber and the second stop consists of the upstream end of a sleeve inserted into the tubular unit.

Another object of the invention are means for reliably guiding the optic fiber inside the tubular unit.

This is achieved by providing a tube stub extending the main tubular unit and of which the bore allows passing either the optic fiber or a guide filament but not both simultaneously.

The description below is of an illustrative but non-restrictive embodiment mode of the invention and in relation to the drawing.

Figure 3:
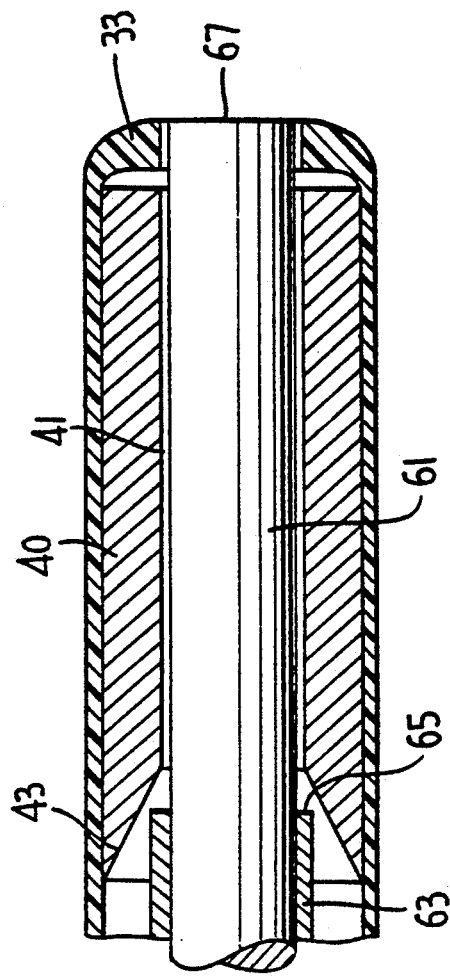
Figure 2:
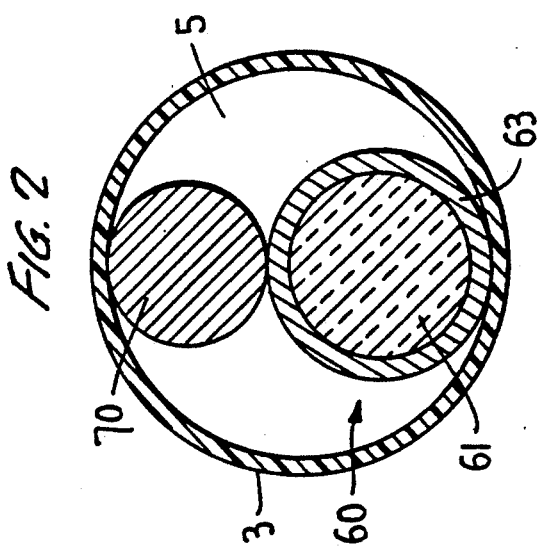

FIG. 1 is a partial view in longitudinal section of the tubular unit constituting the laser catheter of the invention, FIG. 2 is an enlarged view in cross-section along 2—2 of the tubular unit of FIG. 1 shown including an optic fiber and a guide means in the tubular unit, FIG. 3 is a partial view, enlarged and in longitudinal section, of the distal catheter end with the optic fiber in the operational position.

The laser catheter is referenced by 1 and consists of a tubular unit 3 with a longitudinal bore 5 open at both ends. The proximal end, which is omitted, comprises suitable means for hook-up to a laser energy source, to the various supplies in fluids required for the treatment and to the displacement controls of the various apparatus components. The tubular unit is made of a flexible material such as a vinyl polychloride, polytetrafluoroethylene, polyethylene, etc. As shown by FIG. 1, which only shows the distal apparatus end, the tubular unit ends in a terminal tube stub 31 of which the longitudinal bore 51 with a smaller diameter is located in the extension of the bore 5. An intermediary segment 32 joining the tubular unit 3 to the stub 31 tapers through a bore opening 52 of which the diameter decreases progressively from the bore 5 to the bore 51. This opening 52 illustratively is frusto-conical. The tube stub 31 in turn ends on the side opposite the segment 32 in a stopper 33 perforated by an aperture 35 with a diameter at most equal to that of the bore 51. This stopper constitutes the distal catheter end. It may be made of the same material as the tube segment 32 and in that case it is made simply by deforming the tube walls or by molding. It may also consist of another material, for instance a more flexible one such as silicone rubber, and then may be independent of the tube segment 32. This variation relates to in particular cardiac applications, where damage to small vessels during catheter emplacement must be avoided.

Immediately upstream of the stopper 33, a sleeve 40 constricting the bore 51 and made preferably of an x-ray opaque material is present inside the tube stub 31. Stainless steel is a suitable x-ray opaque material. This sleeve subtends a duct 41 communicating between the bore 51 and the aperture 35 and provides an upstream-pointing stop surface 43. Hereafter, the expressions "upstream" and "downstream" relate to the direction of propagation of the light wave in the optic fiber from the proximal end (omitted) to the distal end.

The bore 5 of the tubular unit 3 evinces a sufficiently large diameter to house an optic fiber 60 and a guide element 70 in the manner shown by FIG. 2. This guide element may be a stainless steel wire wound in a helix or any other equivalent element conventionally used to coaxially guide the catheter in the blood vessels.

The bore 51 of the tube stub 31 evinces a diameter large enough to house the guide element or else the optic fiber but not both at the same time. It shall be borne in mind that the optic fiber 60, which is known per se, consists of one fiber or of a bundle of fibers 61 made of a material such as glass or plastic which is capable of transmitting the energy of a laser beam or any other radiation of the same type, and that it is generally clad in a sheath 63. Regarding the guide element 70, it is selected in such a way that its transverse bulk at most be equal to that of the fiber or bundle of fibers 61 when stripped, for reasons elucidated below.

The duct 41 subtended by the sleeve 40 evinces a diameter sufficiently large, as shown by FIG. 3, to allow passing the guide element 70 along which the tubular unit is made to slide as far as the treatment site, or to allow passing the optic fiber 61 stripped of its sheath 63. However, the duct 41 is too narrow to slide through it the complete optic fiber, that is when it is inside its sheath.

Accordingly, FIG. 3 shows the catheter end with the optic fiber in its operational position. The fiber was stripped over a specified length in such a manner that its end 67 is essentially in the plane of the aperture 35 when the end of the sheath, which forms a first stop 65, rests against the stop 43, which is the second. The stop surface 43 slants relative to the tube axis so as to facilitate the insertion of the fiber of the guide filament into the duct 41. However, the slant angle must not be too shallow in order not to degrade the positioning accuracy of the fiber. The angle is selected as a compromise between the two requirements.

Other stop means, both as regards the first stop 65 resting on the optic fiber and the second stop 43 resting on tubular segment are conceivable; furthermore, their location is not restricted to the distal end zone of the catheter.

The first stop 65 is rigidly affixed to the optic fiber and in the embodiment being discussed consists of the end of the optic-fiber sheath; it may consist of any other equivalent means such as a sleeve or ring mounted on the fiber itself.

Preferably the sleeve 40 shall comprise suitable passages for liquids, for instance for a physiological liquid displacing the blood or for a contrast medium for x-ray display of the treatment. For that purpose longitudinal or helical grooves may be fashioned in the wall of the duct 41 or else in the sleeve itself. Such passages are omitted from the Figures.

The sleeve 40 represents a simple embodiment of the catheter end. However, it may be replaced by bosses extending in a generally longitudinal direction and circumferentially spaced so as to provide, in addition to the duct 41, axial or helical passages assisting in the flow of the liquid to be introduced in the treatment zone. In that case the bosses shall be mutually cooperating to define the second stop 43.

A catheter of the invention was actually built, of which the tubular unit evinces an outside diameter of 1.33 mm (CH4) and of which the end tube stub has a diameter of 1 mm (CH3). The duct 41 allows housing an optic fiber 0.45 mm in diameter.

The catheter can be used in different modes of operation depending on the sort of obstruction to be eliminated and the practitioner's preferences.

Illustratively, one operational mode may comprise the following steps:

A. First the guide element 70 is introduced into the blood vessel or cavity until its distal end arrives in the zone where the obstruction which must be treated is located;
B. The tubular unit is coaxially slipped along the guide until its distal end arrives on site;
C. The emplacement of the guide and of the tubular unit can be monitored by fluoroscopy by injecting an x-ray opaque fluid through the bore to display the cavity and its obstruction, using known methods;
D. Once the catheter distal end has been position accurately relatively to the target, and where called for after it has been immobilized by means of a balloon if so equipped, the guide is pulled back a few cm in the bore 5 to free the bore 51;
E. The optic fiber is pushed into the bore 51 until the first stop 65 abuts the second stop 43; thereupon the end of the optic fiber is in place;
F. The lesion is treated by applying the laser energy;
G. Steps A through F are repeated as often as needed to clear the vessel.

The invention is not restricted to the shown embodiment mode and includes all equivalent designs or other additional means available to the expert.

Illustratively and as already mentioned above, the apparatus may include an inflatable balloon whereby the catheter end can be locked relative to the walls of the cavity. The ring-shaped balloon located around the tubular unit is supplied with fluid for its inflation from a conduit inside it. Balloon catheters are well known in the field; they need not be described herein.

Lastly, this technique also may be applied to treatment or display endoscopes.

I claim:

1. A catheter to rid a blood vessel or other duct of a human body of an obstructive matter by ablation using laser energy comprising an optic fiber element, at least one tubular unit having a proximal end, a distal end and a bore along said at least one tubular unit's central axis, said proximal end including means for hook-up to a laser energy source and said distal end including a duct portion therein, wherein the duct portion of said distal end has a diameter approximate to the diameter of said optic fiber element, a first stop is affixed to said optic fiber and a second stop is affixed to said tubular unit, and said first stop and said second stop cooperate with each other to position said optic fiber in a position wherein a first end of said fiber is positioned in said duct portion of said distal end so as to be capable of transmitting light energy through said fiber to an obstructive matter, and said at least one tubular unit further comprises a portion between said distal end and said proximal end in which said bore has a diameter such that when a guide filament is present in said bore with said optic fiber that said optic fiber or said guide filament can pass through said portion between said distal end and said proximal end of said bore singly but not simultaneously.

2. Catheter according to claim 1 wherein said duct portion is constructed and arranged to provide for passage of fluid therethrough when said optic fiber is positioned in said duct portion of said distal end so as to be capable of transmitting light energy through said fiber.

3. Catheter according to claim 1 wherein said at least one tubular unit further comprises another portion between said distal end and said proximal end in which said bore has a diameter such that when a guide filament is present in said bore with said optic fiber that said optic fiber and said guide filament can pass simultaneously through said portion of said bore.

4. Catheter according to claim 1 further comprising an inflatable balloon.

5. Catheter according to claim 1 wherein said distal end is made of a material more flexible than said tubular unit.

6. Catheter according to claim 1 wherein said optic fiber consists of a single fiber or a bundle of fibers made of an optical material clad by a sheath, and said first stop consists of one end of said sheath.

7. Catheter according to claim 1 wherein said first stop consists of a sleeve mounted on said optic fiber.

8. Catheter according to either claim 1, 6 or 7 wherein said duct portion has a lesser diameter than said bore and said second stop consists of an end of said duct portion which joins said bore.

9. Catheter according to claim 8 wherein said duct portion consists of a sleeve mounted inside one end of said bore of said at least one tubular unit.

10. Catheter according to claim 8 wherein said second stop consists of at least one boss present on an inside wall of said bore.

11. Catheter according to claim 1 wherein said portion between said distal end and said proximal end is a first portion, said at least one tubular unit further comprising a second portion between said distal end and said proximal end in which said bore has a diameter such that when a guide filament is present in said bore with said optic fiber that said optic fiber and said guide filament can pass simultaneously through said second portion of said bore, said first portion being joined to said second portion at a third portion of said unit in which said bore has a tapered cross-sectional diameter which allows said bore of said first portion to join said bore of said second portion.

* * * * *